United States Patent [19]

Pike

[11] 3,977,402
[45] Aug. 31, 1976

[54] INJECTION APPARATUS AND METHOD WITH AUTOMATIC ASPIRATION FEATURE

[76] Inventor: William Floyd Pike, 609 W. Iron, Hobbs, N. Mex. 88240

[22] Filed: July 14, 1975

[21] Appl. No.: 593,771

Related U.S. Application Data

[63] Continuation-in-part of Ser. No. 559,961, March 25, 1975.

[52] U.S. Cl. .............................. 128/218 D; 128/221; 128/215; 128/276
[51] Int. Cl.² .................................... A61M 5/00
[58] Field of Search ......... 128/218 D, 218 A, 218 F, 128/218 R, 218 DA, 215, 216, 225, 220, 128/221, 173, 213, 276; 222/389, 390, 394

[56] References Cited
UNITED STATES PATENTS

| | | | |
|---|---|---|---|
| 3,066,670 | 12/1962 | Stauffer | 128/218 F |
| 3,527,212 | 9/1970 | Clark | 128/215 X |
| 3,583,399 | 6/1971 | Ritsky | 128/218 D |
| 3,605,744 | 9/1971 | Dwyer | 128/218 F |
| 3,720,211 | 3/1973 | Kyrias | 128/215 X |
| 3,735,761 | 5/1973 | Hurschman et al. | 128/218 D X |
| 3,788,315 | 1/1974 | Laurens | 128/173 H |

Primary Examiner—John D. Yasko
Attorney, Agent, or Firm—Henry Heyman

[57] ABSTRACT

An apparatus for intramuscular or subcutaneous injection of medications featuring automatic aspiration capability is disclosed herein. In a preferred embodiment the apparatus is completely self-contained, i.e., all components required for injection including antiseptic, antiseptic applicator, sterile needle of appropriate gauge and length, sterile medication in unit dose form, means of automatically inserting the hypodermic needle in tissues of the injection site, unique means of automatic aspiration, and means of automatically injecting said unit dose are contained within the subject invention. An injection method and a method for automatic aspiration are also disclosed herein.

8 Claims, 9 Drawing Figures

INJECTION APPARATUS AND METHOD WITH AUTOMATIC ASPIRATION FEATURE

BACKGROUND OF THE INVENTION

The present invention relates generally to an apparatus and method for administering intramuscular or subcutaneous injection of medications in an automatic manner and this application is a continuation-in-part of application Ser. No. 559,961 filed Mar. 25, 1975 by William F. Pike for INJECTION APPARATUS AND METHOD.

Historically, such injections have been characterized by laborious separate steps which reduce efficient utilization of the working time of professional personnel and others legally entitled to administer parenteral medications. Injections are also characterized by inherent problems and limitations such as the risk of infection, the possibility of injection accidents, needle blow-off with viscous medications, the skill or ineptness of those administering such injections, and, of course, the psychological trauma associated with impending injection and the sight of an exposed hypodermic needle. Relatively little has changed in the art. These objections and others are detailed more completely in pending application Ser. No. 559,961.

Although much importance has traditionally been attached to aspiration prior to intramuscular or subcutaneous injection to insure that the hypodermic needle is not lodged in a blood vessel, only a small percentage of those administering such injections routinely aspirate. This is apparently due to the rarity of striking a blood vessel during such injections and to the time and thought required for aspiration prior to injection.

Considering the foregoing, it would seem that the invention disclosed in pending Ser. No. 559,961 would be both satisfactory and convenient for the majority of those administering intramuscular or subcutaneous injections. However, due to the fact that some insist upon an aspiration feature in automatic syringes, provision is made in the present invention for unique and automatic aspirations which requires little time or care. Therefore a choice will be available to health care specialists, diabetics, and other qualified personnel who wish to use self-contained automatic syringes for the sake of convenience, safety, and conservation of time.

The present invention, then, abrogates all disadvantages and limitations previously cited by providing a simple, uncomplicated, dependable, and self-contained apparatus for automatic and uniform intramuscular injections, in particular, regardless of differences in ability or training of the operator.

SUMMARY OF THE INVENTION

An object of the present invention is to provide a simple self-contained apparatus for essentially automatic intramuscular or subcutaneous injections of medications, said apparatus containing antiseptic, antiseptic applicator, sterile hypodermic syringe of appropriate gauge and length, sterile unit dose of medication, propulsion means for automatic needle insertion in human or other animal tissues, means of automatic aspiration, and propulsion means for injection of said unit dose of medication into tissues of the injection site.

Another object of the present invention is to provide a unique but simple means of automatic aspiration such that injection accidents may be reduced still further in number. Although evacuated puncturable chambers of various types and designs have been used for many years to effect aspiration in medical devices, the unique means of aspiration in the present invention is to be preferred since it is both more compatible with the objects of the present invention and more economical. In addition, it requires fewer control means for correct operation.

Yet another object of the present invention is to provide an apparatus of unit dose capability for intramuscular or subcutaneous injection from less than 1 cubic centimeter to 10 or more cubic centimeters capacity.

A further object of the present invention is to insure single use of the apparatus so as to (1) prevent unauthorized and repeated use, (2) reduce the risk of infection associated with injections, and (3) reduce pilferage of controlled injectable substances by facilitating inventories and supervision of personnel in institutional situations.

Another object of the present invention is to provide an injection apparatus of pleasing appearance and concealed contents, including hypodermic needle, thereby reducing the level of apprehension in recipients, particularly pediatric patients.

Still another object of the present invention is to enable individuals unskilled in the art to inject themselves or others in a safe and convenient manner in truly life-threatening or painfully disabling situations in which immediate care by a physician is impossible, said administration dictated by prior agreement with a physician or in accordance with special provisions of statutes which may be enacted to reduce the high mortality rate of e.g., myocardial infarctions by injection of medications generally considered beneficial in such episodes.

Yet another object of the present invention is to provide an apparatus to enable diabetics whose condition cannot be controlled by a diet or oral medications to safely and conveniently inject themselves with one of the insulin preparations in unit dose form prescribed by a physician. It should be noted that some diabetics have poor vision due to their condition and, using current injection techniques, frequently draw up and inject an incorrect volume of insulin which may result in most serious consequences. Unit dosage, prescribed according to their own particular conditions and changed when necessary, would prevent such mishaps when used in conjunction with the present invention.

A futher object of the invention is to provide an apparatus which eliminates antibiotic aerosols and therefore largely prevents development of antibiotic-resistant strains of bacteria.

Another object of the present invention is to provide an apparatus which requires no assembly under adverse or emergency conditions and which is therefore immediately available for use in hospital emergency rooms.

Still another object of the present invention is to provide a means whereby a chemical substance or chemical substances contained within subject invention exerts sufficient fluidic pressure to insert a hypodermic needle into tissues to a desired depth and which then, following aspiration, forces a particular dose of medication from container means into the tissues at a desired rate regardless of viscosity of the medication.

A further object of the present invention is to provide an apparatus which precludes the possibility of premature injection of medication and which also precludes the possibility of propellent fluid entering the tissues.

Yet another object of the present invention is to provide an injection method having the foregoing features.

These objectives and other objectives and features to become apparent hereinafter are attained by an apparatus or modification of an apparatus constructed in accordance with the present invention.

In a preferred embodiment of the present invention a tear tab is removed thereby removing the covering of the antiseptic applicator from one end of the apparatus. While still attached to the apparatus, the antiseptic applicator is rubbed over the injection site and is then removed from the apparatus. The apparatus is placed with the needle aperture against the skin, following which a control septum is depressed which in turn activates a cartridge containing fluid under pressure. Sudden expansion of said fluid forces a medication-containing cartridge of specialized construction against one end of a double-ended hollow needle, said end penetrating a septum of the medication-containing cartridge and affording a channel through which medication will pass from cartridge to tissues at the injection site.

The now-coupled needle assembly and medication cartridge are propelled through the assembly tube of the apparatus and are stopped by contact with the assembly tube base. At this time the lower needle of the double-ended needle assembly has passed through an exit port in the assembly tube base and has penetrated the tissues to a depth dictated by the length of the lower needle. Automatic aspiration is effected by magnetic means in a manner to be described in detail subsequently. Upon completion of aspiration a medication cartridge piston is exposed to increased fluidic pressure thereby forcing the plunger to deposit the medication in the tissues.

The needle is withdrawn from the tissues by pulling upward on the assembly tube without lateral motion. The apparatus is inspected to insure that the medication has been deposited in the desired site and is then discarded.

DETAILED DESCRIPTION

Figure 1:
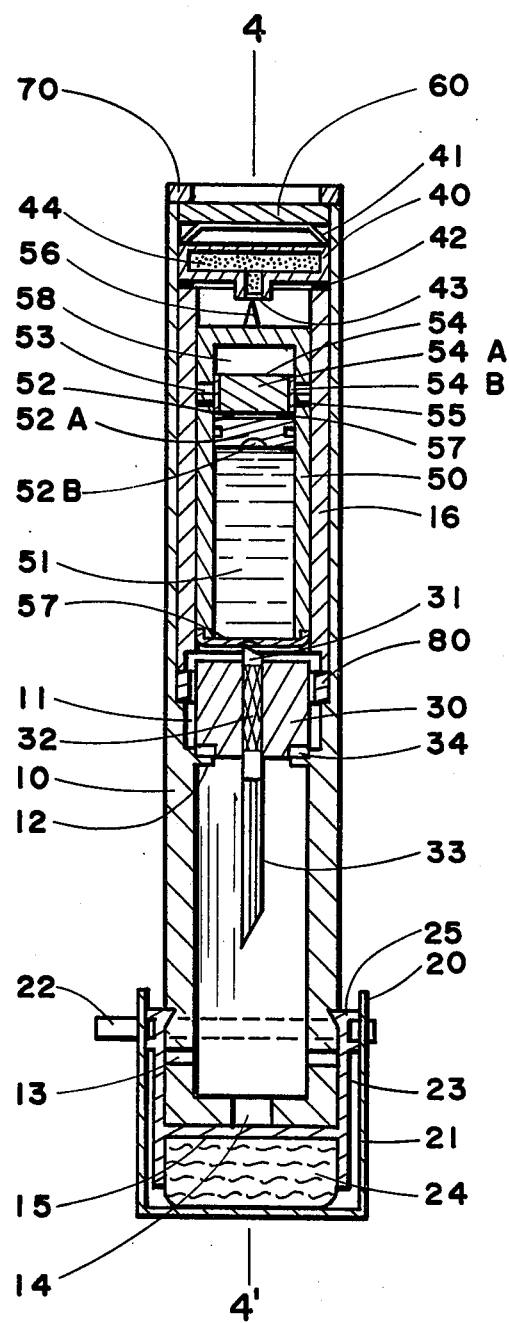
FIG. 1 illustrates an enlarged side elevational view, in cross section, of the components of the apparatus constituting the present invention.
Figure 2G:
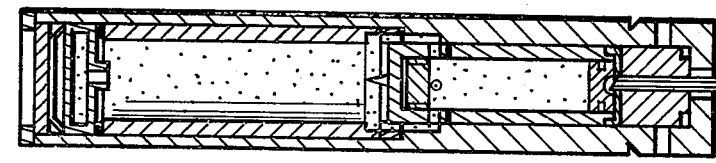
FIG. 2 A through FIG. 2 G illustrate a series of side elevational views in cross section of the present invention to approximate scale for 2 cubic centimeters of medication and depicts the sequence of events from activation of propulsion means in FIG. 2 A through completion of medication injection in FIG. 2 G.
Figure 2F:
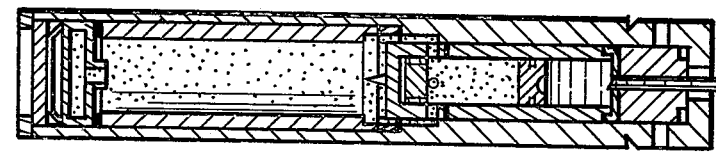
Figure 2E:
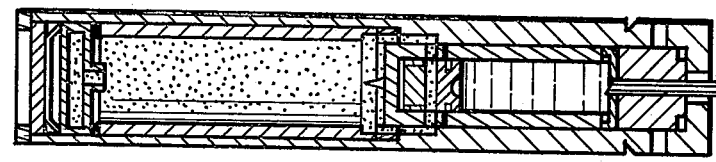
Figure 2D:
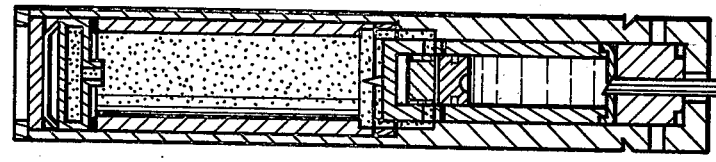
Figure 2C:
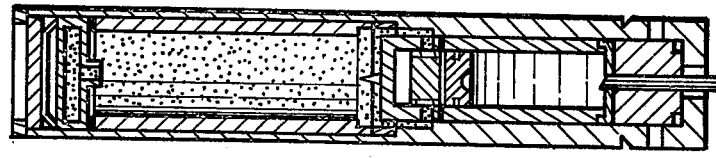
Figure 2B:
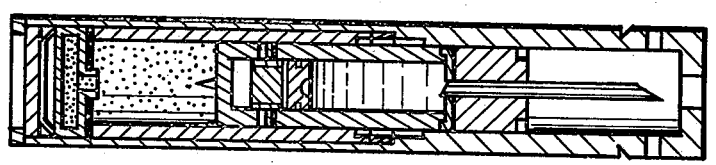
Figure 2A:
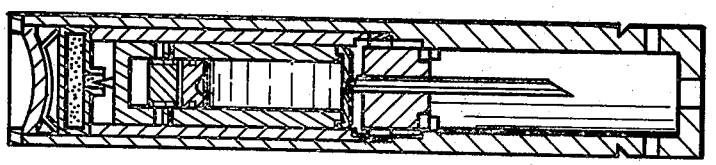

Referring to the FIGURES, wherein like components or features are designated by like reference numerals throughout, attention is directed to FIG. 1 which depicts in enlarged cross sectional view the components and features of the present invention. Although resembling FIG. 1 of previously submitted disclosure Ser. No. 559,961, unique components and features which are distinctly different, thereby constituting a separate invention, are contained in the present invention as will be described subsequently.

Figure 3:
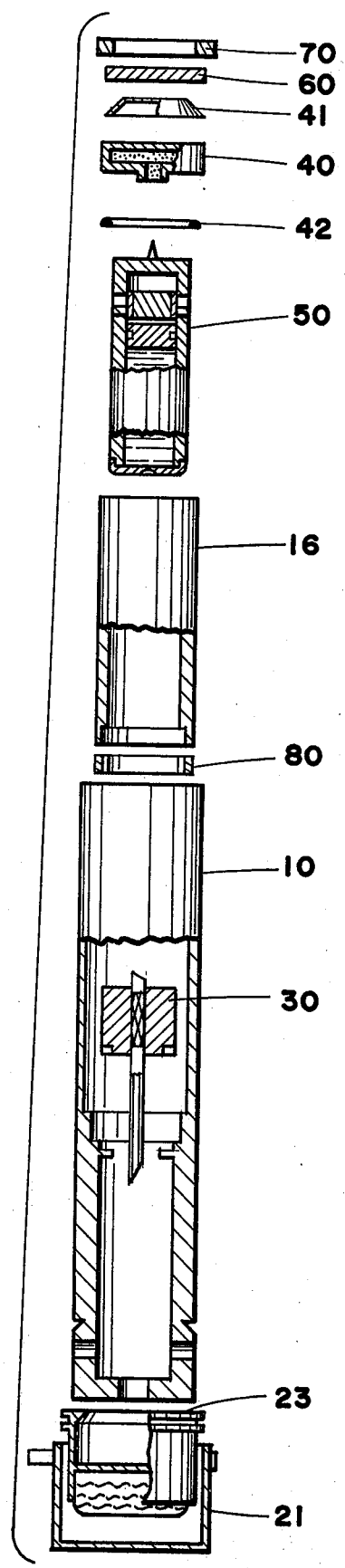
FIG. 3 illustrates a side elevational view in cross section of the individual components or component assemblies depicting thereby, and as discussed subsequently, a suggested means of preparation and assembly of the apparatus constituting the present invention.

As will be noted in reference to FIG. 1 and FIG. 3, the apparatus consist of an assembly tube 10 within which or attached thereto are separate components now to be described in part.

Viewed along the line 4 — 4', activation septum 60 is recessed and sealed in place by activation septum seal 70. Plastic spring 41 or other suitable means distributes mechanical pressure over the periphery of propellent assembly 40 when activation septum 60 is depressed by digital pressure, as will be described subsequently.

Propellent assembly 40 containing fluid 44 under pressure is supported by flexible annular support 42, the latter being supported by contact with inner sleeve 16.

Although this configuration is suggested for propellent assembly 40 in relation to the remainder of the apparatus for the purpose of consistency with the above mentioned prior disclosure, it must be emphasized that other unique arrangements to supply propulsion means for subject invention may be effected for economy, convenience, or other considerations. For example, propellent assembly 40 may be reduced in diameter, inverted, fluid channels incorporated and attached to, or be supported by, medication cartridge assembly 50 so that the propellent assembly itself is capable of moving through a portion of assembly tube 10. In such case propellent seal perforator 56 would in turn be inverted and become part of a disc-like structure between activation septum 60 and flexible annular support 42. Indeed, such an arrangement may be preferred by some manufacturers since the added mass of propellent assembly 40 in position superior to that of medication cartridge assembly 50 would further accelerate the latter, thereby reducing fluidic pressure required for operation of subject invention and possessing the added advantage of a reduction in back pressure.

Furthermore, in yet another possible and in some cases desirable arrangement and example, propulsion means for the invention may be obtained by connecting the upper interior of assembly tube 10 to an external disposable, reusable, or other pressurized source which may be either fixed or portable.

Additionally, it must be noted that although compressed gas or volatile liquid under pressure is most desirable due to economic considerations, fluid 44 may have its origin in reactive solids, solids which undergo extremely rapid sublimation, or chemicals which, when mixed immediately prior to injection, produce sufficient gas to accomplish injection.

Continuing downward along the line 4 — 4' of FIG. 1, within inner sleeve 16, which in turn is surrounded by a portion of assembly tube 10, is medication cartridge assembly 50 which is, as will be seen in subsequent discussion and FIGURES, of unique design and specialized construction. Attached propellent seal perforator 56 is in tangential contact with propellent seal and exhaust port 43 of propellent assembly 40. Medication cartridge assembly 50 is supported by contact of septum 57 with upper needle 31 of needle assembly 30 which in turn is supported by contact with shear tabs 12.

Particular attention is directed to serrated magnet 80, supported within assembly tube 10 by a shoulder thereof. Although referred to as serrated magnet 80 for convenience throughout the disclosure, the magnet itself need not be serrated but may instead enclose and seal a serrated nylon or other bushing through which fluid 44 will pass as it enters fluid channel 11, as it does in the preferred embodiment.

Attached antiseptic applicator assembly 20 is affixed to the lower portion of assembly tube 10 by applicator support retainer 25, the latter engaging a circumferential depression of assembly tube 10 so as to effect closure between assembly tube 10 and external surroundings thereby assuring maintenance of sterility within assembly tube 10.

Enclosing applicator support 23 and antiseptic applicator 24 is covering 21, which is sealed to applicator support retainer 25 by means of tear tab 22 so that an airtight seal is obtained to retard evaporation of the antiseptic in antiseptic applicator 24.

Brief departure is necessary in order to summarize events concerning the antiseptic applicator assembly 20 which does not appear in FIG. 2 A through FIG. 2 G, said events having been described in detail in the previously cited disclosure, Ser. No. 559,961. Covering 21 is removed by the operator by means of tear tab 22, following which assembly 10 is used as a supportive handle to apply antiseptic contained in antiseptic applicator 24 to the intended injection site. Antiseptic applicator assembly 20 is then removed by pulling applicator support 23 along the line 4 — 4' so as to dislodge applicator support retainer 25 from the circumferential depression in assembly tube 10.

Turning now to FIG. 2 A through FIG. 2 G, shown approximately to scale for 2 cubic centimeters of medication, the operative sequence of subject invention will be discussed in detail.

In FIG. 2 A the base of assembly tube 10 is in intimate contact with skin at the injection site. Activation septum 60 has been depressed by digital pressure forcing plastic spring 41 to apply pressure upon the upper periphery of propellent assembly 40. As a result of said pressure propellent assembly 40 depresses flexible annular support 42 thus effecting penetration of propellent seal 43 by propellent seal perforator 56. Said perforation affords a pathway for compressed fluid 44 to exit through propellent seal and exhaust port 43.

In FIG. 2 B, release of fluid 44 to the upper interior of inner sleeve 16 is restricted by the presence of medication cartridge assembly 50. Sudden expansion of fluid 44 above medication cartridge assembly 50, however, forces said assembly to move downward within inner sleeve 16 and thence assembly tube 10 along the line 4 — 4' of FIG. 1, forcing penetration of septum 57 by upper needle 31 thereby providing a pathway for medication 51 to fill the cannula of needle assembly 30, concomitantly shearing shear tabs 12 which are retained in shear tab retention depressions 34 of needle assembly 30.

It should also be noted that as coupled needle assembly 30 and medication cartridge assembly 50 descend along the line 4 — 4' of FIG. 1, air in the interior of assembly tube 10 is forced through air exhaust perforations 13 so that continued descent of the coupled assemblies is not impeded by air compression.

Also with respect to FIG. 2 B it must be noted that passage of the now-coupled assemblies through upper sleeve 16 and assembly tube 10 is sufficiently rapid that, as cartridge magnet 54 A approaches and passes through the opening in serrated magnet 80, no response of cartridge magnetic piston assembly 54 occurs due to its inertia. Only when movement ceases, i.e., only when the inferior surface of needle assembly 30 is firmly seated against the superior surface of assembly tube base 15 does magnetic attraction between cartridge magnet 54 A and serrated magnet 80 become appreciable. Even then the response is relatively slow, but continuous, until further movement of cartridge magnetic piston assembly 54 along the line 4' — 4 is no longer possible, as will be seen subsequently.

Attention is now directed to FIG. 2 C in which it may be seen that coupled needle assembly 30 and medication cartridge assembly 50 have undergone maximum displacement with the inferior surface of needle assembly 30 firmly seated against the superior surface of assembly tube base 15. As will also be evident from consideration of FIG. 2 C, lower needle 33 has achieved maximal penetration of tissues at the injection site at this time.

Although compressed fluid 44 has flowed into fluid channel 11 in FIG. 2 C, access to the interior of medication cartridge assembly 50 via medication cartridge perforations 53 is prevented by the presence therein of cartridge magnetic piston assembly 54, the latter comprised of cartridge magnet 54 A and cartridge seal 54 B. The presence of cartridge magnetic piston assembly 54 within medication cartridge assembly 50 serves, then, to momentarily prevent fluid 44 from exerting pressure upon cartridge medication piston 52 so that medication 51 is not immediately injected into the tissues.

Also with respect to FIG. 2 C and reference to FIG. 1 it should be noted that cartridge magnetic piston assembly 54 is separated from cartridge medication piston 52 by cartridge lower space 57. The importance of cartridge lower space 57 and cartridge upper space 58 will become apparent in subsequent discussion.

In FIG. 2 D, overlap of magnetic fields of opposite polarity of cartridge magnet 54 A and that of serrated magnet 80 results in attraction between the two magnets. Serrated magnet 80, in position between inner sleeve 16 and a shoulder of assembly tube 10 is in a fixed position and therefore can undergo no displacement. However, cartridge magnetic piston assembly 54 containing cartridge magnet 54 A is capable of displacement within medication cartridge assembly 50 so that it responds to the magnetic field from serrated magnet 80 and begins upward movement within medication cartridge assembly 50 along the line 4' — 4 of FIG. 1. As cartridge magnetic piston assembly 54 moves upward it initiates compression of gaseous molecules in cartridge upper space 58. In this FIGURE, however, medication cartridge perforations 53 remain momentarily sealed thereby retarding entry of fluid 44 and resultant deposition of medication 51.

Upward movement of cartridge magnetic piston assembly 54 creates a partial vacuum in cartridge lower space 57. The vacuum produced suctions cartridge medication piston 52 upward along the line 4' — 4 of FIG. 1. The result is automatic aspiration, thereby allowing the operator to determine by inspection of medication 51 if the aperture of lower needle 33 is lodged in a blood vessel. If blood appears in medication 51 lower needle 33 must immediately be removed from the tissues so as to prevent deposition of medication 51 in the vasculature by pulling upward on assembly tube 10 and quickly inserting lower needle 33 into an immediately available container or other external deposition site, e.g., antiseptic applicator 24, such that medication 51 is expelled into and is entrapped by said container.

It must be emphasized that blood is rarely noted during manual aspiration prior to intramuscular or subcutaneous deposition of medication using current injection techniques. It is so rare, in fact, that most operators bypass the aspiration step and proceed with medication injection. Although extremely rare in number, injection accidents frequently lead to serious or fatal reactions to the injected medication. Proper use of subject invention, however, insures automatic aspiration regardless of the opinion or preference of the operator thereby leading to even fewer injection accidents. The time required for aspiration to be completed may be controlled most easily by controlling the gauss ratings of cartridge magnet 54 A and serrated magnet 80. In any event, provision should be made for a delay of a minimum of two seconds to allow reaction time for the operator to intervene should intervention prove necessary.

Continuing with FIG. 2 D and assuming that routine injection is being effected, i.e., that no blood appears in medication 51 following aspiration, attention is briefly directed to characteristics of the operational sequence within medication cartridge assembly 51 heretofore not discussed in detail. As cartridge magnetic piston assembly 54 continues to move upward along the line 4' — 4 of FIG. 1, compression of gaseous molecules entrapped in cartridge upper space 58 increases, thereby gradually reducing the acceleration of cartridge magnetic piston assembly 54, i.e., although the magnetic attractive force between serrated magnet 80 and cartridge magnet 54 A is appreciable, continued compression of gas in upper space 58 slows and, as will be seen subsequently, eventually stops upward progress of cartridge magnetic piston assembly 54.

Furthermore, as pressure continues to decrease in cartridge lower space 57 due to upward movement of cartridge magnetic piston assembly 54, the intensified vacuum exerts sufficient suction to effect upward movement of cartridge medication piston 52 along the line 4' — 4 of FIG. 1. However, due to the relatively rapid magnetic response between movable cartridge magnet 54 A and fixed serrated magnet 80, and the inertial lag of cartridge medication piston 52, the distance between the two pistons increases momentarily as may be seen in FIG. 2 D.

Attention is now directed to FIG. 2 E. As will be noted in examining the FIGURE, cartridge magnetic piston assembly 54 has undergone maximum vertical displacement along the line 4' — 4 of FIG. 1 due to the presence of compressed gas in cartridge upper space 58. Since both the gas pressure retarding further progress and the magnetic attractive force promoting further progress of cartridge magnetic piston assembly 54 remain constant, no additional movement or reciprocation of magnetic piston assembly 54 is possible.

Furthermore, this FIGURE illustrates that medication cartridge perforations 53 are no longer blocked by cartridge seal 54 B. Therefore fluid 44, previously restricted to the exterior of medication cartridge assembly 50, is free to pass through medication cartridge perforations 53 into cartridge lower space 57 and exert fluidic pressure upon the superior surface of cartridge medication piston 52.

FIG. 2 F is essentially a mid-position view depicting injection of medication 51, i.e., fluid 44 has exerted pressure upon the superior surface of cartridge medication piston 52 thereby forcing medication 51 through the cannula of needle assembly 30 and into the tissues of the injection site.

In FIG. 2 G, injection of medication 51 has been completed since the inferior surface of solid portion 52 A of cartridge medication piston 52 has contacted the superior surface of septum 57. Therefore, it may be seen that the volume of medication 51 prior to injection is defined by the inferior surface of cartridge medication piston 52 and the superior surface of septum 57. It must be noted that upper needle 31 has entered cartridge piston depression 52 B, but has not penetrated solid portion 52 A of cartridge medication piston 52. Therefore fluid 44 is precluded from entering the cannula of needle assembly 30, i.e., no propellent may be accidentally injected into the tissues of the injection site.

Lower needle 33 is withdrawn from the tissues without lateral motion by pulling upward on assembly tube 10, although automatic retraction of lower needle 33 may be effected by rather minor modification of the present invention.

Following inspection of medication cartridge assembly 50 to verify injection of medication 51, the apparatus and antiseptic applicator assembly 20 are discarded. It should be noted, however, that although it is generally desirable for reasons previously cited to produce subject invention in disposable form, the present invention may be modified to render it reusable for applications in veterinary medicine in particular.

Having discussed subject invention both generally and in detail, attention is now directed to FIG. 3 in which a suggested means of preparation and assembly of the components of subject invention is depicted. Periodic referral to FIG. 1 will be necessary throughout the remainder of the discussion, however.

As previously noted, concealment of the contents of the present invention from recipient's vision is desirable and may inexpensively be effected by spray-painting the exterior surface of assembly tube 10 after a narrow strip extending the length of the assembly tube has been masked, i.e., prior to painting, sterilization and assembly. Many paints in attractive colors are commercially available for rendering clear plastic opaque or translucent. Pigmented plastics or other polymeric substances may also be used in construction of assembly tube 10 although they are generally more expensive and would be less desirable in human medicine since medication cartridge 50 must be inspected prior, during, and subsequent to injection.

In addition to rendering assembly tube 10 opaque or translucent for purposes of concealment of contents, such treatment has other advantages such as shielding medication 51 from potentially detrimental incident light as well as affording color-coding capability to identify the general type of medication contained therein. One or more narrow bands of contrasting color may aid in rapid determination of the actual quantity of medication comprising the unit dose contained within subject invention.

It must be noted, however, that reliance on color coding alone is insufficient since those authorized to use hypodermic syringes may experience difficulty in differentiating subtle color changes.

The masking referred to above, extending the length of assembly tube 10, may further serve to identify the medication contained therein by appropriate labeling although, of course, the exterior painted portion could also be labeled. In either case when the masking is removed immediately prior to injection the operator, upon reading the labeled portion, is assured that the medication contained therein is of the specific type and dosage which was prescribed. (Many patients have experienced severe or fatal reactions to parenteral medications due primarily to the fact that they received the wrong medication or the correct medication in incorrect dosage.)

Continuing with brief consideration and discussion of other pertinent features or components of subject invention, attention is directed to medication cartridge assembly 50. It will be seen in FIG. 1 that the casing of this assembly may be divided into two portions which are connected to each other by junction 55, said junction effected by any convenient means well known in the arts. The superior portion of the cartridge casing may be composed of a formed polymer alone or a polymer-metal combination. The inferior portion of the cartridge casing, however, containing medication 51 which could conceivably react with many polymeric materials upon prolonged storage, may be composed of traditionally used shatter-resistant glass or other suitable chemically-resistant material.

However, it should be noted that two-piece casing construction is not essential to the invention, i.e., single unit casing may be utilized provided that suitably resistant material be used. Chemically inert polytetrafluoroethylene as an interior coating for standard polymers or as total casing material, coupled with the added advantage of its low coefficient of friction, is an obvious choice.

Preparation of medication cartridge assembly 50, i.e., insertion of cartridge magnetic piston assembly 54, cartridge medication piston 52, attachment of septum 57 and loading of the correct quantity of medication 51 may be effected by any means known in the art provided that the sterility of medication 51 is insured.

Needle assembly 30, preferentially a convenient plastic cylinder within which is embedded a double-ended hollow needle of siliconized stainless steel held in place by knurled surface 32, should be surface coated with a material possessing a low coefficient of friction such as polytetrafluoroethylene.

Cartridge magnet 54 A and serrated magnet 80, although not available commercially in the sizes required for production of subject invention, may be manufactured very cheaply. In mass production each magnet should cost a maximum of 2 cents based upon current catalog prices of similarly shaped magnets of similar gauss ratings. The magnets may be of any type, e.g., Alnico, ceramic, etc., although ceramic magnets, due to their low density and high resistance to demagnetism, are preferred. Since the volume of the cannula within needle assembly 30 is quite small, very little aspiration capability is actually required to determine if lower needle 33 has penetrated a blood vessel. It follows, particularly in view of experimentation using a similar arrangement and system, that a small displacement of cartridge magnetic piston assembly 54 along the line 4' — 4 of FIG. 1 produces sufficient vacuum to suction cartridge medication piston 52 along the same line such that aspiration is effected, as will also be seen in FIG. 2 C through FIG. 2 E. Strong magnets, therefore, are not required.

Although previous discussion was confined to two magnets whose fields are oppositely oriented, i.e., of opposite polarity during aspiration, it may be possible to use one magnet with the other responding member being composed of a suitable ferrous metal which has not been magnetized.

It is also possible, of course, to employ a modification of the present invention to effect aspiration by magnetic repulsion rather than magnetic attraction. For example, a fixed magnet similar to serrated magnet 80 but without serrations could be fixed in position below fluid channel 11 to repel cartridge magnet 54 A and therefore cartridge magnetic piston assembly 54 so as to effect aspiration automatically due to like orientation of magnetic fields. This would eliminate the necessity for serrations or a serrated bushing in the fixed magnet and would have the added advantage of simplification of design of fluid channel 11 and would result in less impediment to flow of fluid 44.

It must be reemphasized that fluid 44 providing propulsion means in subject invention may have its origin in (1) compressed gas contained within propellent assembly 40 or a modification of propellent assembly 40 as described in a preferred embodiment, or by slight alteration of design, have its origin in (2) a liquid of high vapor pressure, (3) a solid such as benzoyl peroxide, or a mixture of solids, which undergoes decomposition to gaseous products when sufficiently agitated, (4) a solid which undergoes rapid sublimation, or (5) two or more chemicals which when suitably mixed at the time of injection produce gas in quantity to insure sufficient pressure for correct operation of subject invention as previously described.

As noted in a preferred embodiment compressed gas, such as, e.g., carbon dioxide is used. Propellent assembly 40 need be no larger than depicted in FIG. 2 A through FIG. 2 G and, in fact, may be smaller. Commercial carbon dioxide cartridges such as those used to inflate life jackets or propel models, for example, contain approximately 1000 times the gas volume needed to fill the inner volume of assembly tube 10 and medication cartridge assembly 50. For essentially instantaneous needle insertion and subsequent injection of 2 cubic centimeters of medication, it is estimated that 3 to 6 atmospheric pressure will be required. Greater or lesser pressures may be used depending upon the volume of medication to be injected and its viscosity.

All components should be sterilized by exposure to a gas such as ethylene oxide, which is toxic to microorganisms, and then assembled under aseptic conditions with additional sterilization stages where necessary. One logical sequence of assembly of subject invention components is depicted in FIG. 3.

Finally, it should be emphasized that subject invention is not restricted to relative sizes or thicknesses depicted in the FIGURES but may be prepared in any desirable dimensions.

I claim:

1. An intramuscular injection system comprising:
   a. housing means
   b. needle means in said housing mounted for linear movement in a first direction from a retracted position in the housing to a position protruding forwardly out of said housing,
   c. linearly movable chemical medication chamber means in said housing having a rupturable portion in alignment with said needle means such that said needle means will rupture said medication chamber means upon selective relative movement of said needle and medication chamber means, d. fluid propulsion means adapted to effect said selective relative movement of said needle means and medication chamber means and to effect linear movement of said needle means between said retracted and protruding positions, and e. aspirating means for automatically creating a partial vacuum in said medication chamber means after said needle has been moved into its protruding position.

2. The injection system of claim 1 wherein said aspirating means includes piston means within said medication chamber means and motive means for moving said piston means in an opposite direction to said first direction to create said partial vacuum.

3. The injection system of claim 2 wherein said piston means includes first and second separate component parts which are moved in unison in said second direction by said motive means, said second part subsequently being movable in said first direction by said fluid propulsion means to force medication from said medication chamber means through said needle means.

4. The injection system of claim 3 wherein said motive means includes magnetic means for attracting said first piston part in said second direction.

5. The injection system of claim 4 further including means for selectively directing said fluid propulsion means in between said first and second piston parts after said parts have been moved in said second direction.

6. A method of injecting medication comprising the steps of:
 1. fluidically moving a rupturable medication chamber into an end of a hypodermic needle so that the needle penetrates the chamber,
 2. fluidically advancing the medication chamber and needle into the object to be medicated,
 3. automatically creating a partial vacuum in said needle, and
 4. subsequently fluidically forcing medication from said chamber, through said needle and into the object to be medicated.

7. The method of claim 6 wherein said step of automatically creating a partial vacuum is carried out by moving a piston means within said chamber to lower the pressure at the end of said needle which has penetrated said chamber.

8. The method of claim 7 including the steps of providing magnetic means to effect movement of said piston means.

* * * * *